(12) United States Patent  (10) Patent No.: US 7,998,218 B1
Brown  (45) Date of Patent: Aug. 16, 2011

(54) MODULAR ORTHOPEDIC IMPLANT (75) Inventor: David R Brown, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 1568 days.

(21) Appl. No.: 11/049,226

(22) Filed: Feb. 2, 2005

(51) Int. Cl.
*A61F 2/38* (2006.01)

(52) U.S. Cl. ............... 623/20.35; 623/20.15; 623/20.14; 623/20.34; 623/20.36; 623/22.11

(58) Field of Classification Search .................. None
See application file for complete search history.

(56) References Cited

U.S. PATENT DOCUMENTS

| | | | |
|---|---|---|---|
| 4,676,797 A * | 6/1987 | Anapliotis et al. ......... | 623/23.45 |
| 4,938,768 A | 7/1990 | Wu | |
| 5,008,736 A | 4/1991 | Davies et al. | |
| 5,030,238 A | 7/1991 | Nieder et al. | |
| 5,032,130 A | 7/1991 | Schelhas et al. | |
| 5,352,227 A | 10/1994 | O'Hara | |
| 5,917,399 A | 6/1999 | Ishii | |
| 6,102,956 A | 8/2000 | Kranz | |
| 6,300,818 B1 | 10/2001 | Mao | |
| 6,307,282 B1 | 10/2001 | Yu et al. | |
| 6,428,578 B2 | 8/2002 | White | |
| 6,447,549 B1 | 9/2002 | Taft | |
| 6,613,092 B1 | 9/2003 | Kana et al. | |
| 6,824,566 B2 | 11/2004 | Kana et al. | |
| 6,866,683 B2 * | 3/2005 | Gerbec et al. ............. | 623/18.11 |
| 7,435,263 B2 * | 10/2008 | Barnett et al. ............. | 623/19.12 |
| 2003/0139818 A1 | 7/2003 | Rogers et al. | |
| 2003/0151860 A1 | 8/2003 | Bryan | |

FOREIGN PATENT DOCUMENTS

FR 2 651 118 3/1991

* cited by examiner

*Primary Examiner* — Corrine M McDermott
*Assistant Examiner* — Christopher D Prone
(74) *Attorney, Agent, or Firm* — Harness, Dickey (57) ABSTRACT

A modular implant system operable to implant into a selected portion of the anatomy. The modular implant system may include an adaptor to allow for interconnection of disparate connection portions to allow for connecting a plurality of connection types. Expanding the modularity of an implant system by allowing interconnection of a plurality of modular implant systems.

25 Claims, 8 Drawing Sheets

MODULAR ORTHOPEDIC IMPLANT

FIELD

The present teachings relate generally to a prosthesis system allowing for interconnection of a plurality of components, and relates particularly to a modular prosthetic system.

BACKGROUND

The human anatomy, or any anatomy, generally includes a plurality of systems. These systems allow the body to perform a variety of functions, such as mobility, support, and the like. Various systems include the skeletal system, the muscular system, the nervous system, and the like. Generally, the anatomy is operable to perform a variety of functions with little difficulty. For example, the human anatomy generally allows a person to move substantially pain free and without need of external support. Nevertheless, various portions of the anatomy, such as various bony or skeletal portions, may become damaged or inoperable for various reasons, such as injury, disease, degradation, or the like.

It is generally known that various implants, including prosthesis to replace various portions of the anatomy, can be used to replace those portion of the anatomy that have become damaged or inoperable for various reasons. Prosthesis may include those that replace various joint portions, replace various bony portions, reattach or reconnect various soft tissues, or any appropriate prosthesis. These prostheses may be implanted according to various techniques to allow for a substantially or anatomical motion of the anatomy after implantation.

These prostheses may be formed in any appropriate manner and may be generalized for ease of production and inventory. The generalized prostheses may be allowed to fit in a majority of the population with little augmentation or change. These general prostheses may be used by a user, such as a surgeon, to replace or repair most maladies. Prostheses may be specialized for various cases, depending upon a particular person. However, the specialized prostheses may generally require additional working, additional inventory, and other considerations. Nevertheless, they may provide for a substantial advantage in various cases.

Prostheses may also be modular for various applications. For example, modular prostheses may be easy to implant or easier to implant in various applications. Modular prostheses may also allow for an amount of customization without requiring a specific prosthesis to be made for an individual. Various portions of the prostheses may be provided in various sizes, configurations, and the like for selection and interconnection by a user, such as a surgeon. The plurality of pieces may allow for the user to select a configuration that may best fit a selected patient without requiring an entire prosthesis to be formed specifically for the single patient. These various portions may interconnect with various mechanisms, such as tapers, threads, and the like. Nevertheless, the various modular portions may generally be designed or allowed to interconnect only with a selected set or composition of modular portions. Therefore, a modular system may only be interconnectable with other portions of the same system and not allow for an intermingling of various modular systems. The unique systems can restrict a surgeon's ability for using a modular system to specialize a selected prosthesis for a patient.

Connectors have been provided in the art that allows a simple connection between two previously developed implant systems. The connector may be used to allow the connection of two parts of an implant while the two parts of the implant may have been dissimilar or not otherwise connectable. In this regard, the different systems each have a different connection size and the prior art connectors allow the dissimilar modular systems to be interconnected. For example, the connector may be the only allowable connection between two modular systems. Other prior art connectors have been provided that allow dissimilar implant systems to be interconnected in a revision type procedure.

During the revision procedure and implant portion may be selected to remain in place while other modular portions are connected relative thereto. The revision procedure that requires a bone resection may require a bone replacement stem, not necessary during the primary procedure. Thus the prior art connectors may be provided to interconnect the bone replacement implant and the remaining prosthetic portions that were previously implanted, where each have dissimilar connection systems.

There is a need, however, to provide even further options to a surgeon or user attempting to connect different modular implant systems. Providing a single connector has limitations in that only specific systems can be interconnected, and generally in only a single orientation. There is a desire to provide further connectors that may be used to interconnect systems in a plurality of manners. Further, it may be useful to provide a plurality of connectors that may be used together to interconnect different modular systems.

SUMMARY

A kit can be provided including a plurality of connectors for interconnecting a plurality of modular systems. The kit can be provided with a plurality of connectors to provide many options to a user to interconnect a modular system. The connections may be both anatomically acceptable and/or include a secondary locking element.

According to various embodiments a method of implanting an implant into an anatomy is disclosed. The method can include assembling a first portion of an implant assembly including interconnecting a first member and a second member having interconnectable connections portions of a first connection region type and positioning the first portion into a portion of the anatomy in a first procedure. The method can also include assembling a second portion of an implant assembly including interconnecting a third member and a fourth member having interconnectable connections portions of the first connection region type and positioning the second portion into a portion of the anatomy in the first procedure. The method can also allow interconnecting the first portion and the second portion, wherein at least one of the first member or the second member have a second connection region type and at least one of the third member and the fourth member have a connection portion interconnectable with the second connection region type. The first connection region type and the second connection region type can be different.

According to various embodiments a modular implant system for being positioned in an anatomy is disclosed. The system can include at least four connectors, wherein each of the four connectors include a first end and a second end. At least two of the connectors can interconnect to form a connector assembly. A first implant member can be positioned in the anatomy and a second implant member can replace a portion of the anatomy when positioned in the anatomy. The first implant member and the second implant member can be implanted into the anatomy and interconnected with the connector assembly. Also, the first end and the second end of each of the connectors can have a different connection region type.

According to various embodiments a connector kit for connecting various portions of an implant is disclosed. A first connector can have a first end and a second end, wherein each of the first end and the second end define a connection region that is different, but wherein the connection region of at least the first end or the second end defines at least a portion of an anatomically acceptable connection region. A second connector can have a first end and a second end, wherein each of the first end and the second end define a connection region that is different, but wherein the connection region of at least the first end or the second end defines at least a portion of an anatomically acceptable connection region. A third connector can have a first end and a second end, wherein each of the first end and the second end define a connection region that is different, but wherein the connection region of at least the first end or the second end defines at least a portion of an anatomically acceptable connection region. Also, a fourth connector can have a first end and a second end, wherein each of the first end and the second end define a connection region that is different, but wherein the connection region of at least the first end or the second end defines at least a portion of an anatomically acceptable connection region. Generally, at least two of the first connector, the second connector, the third connector, or the fourth connector can be interconnected to form a connector assembly for use in an implant to be positioned in the anatomy.

Further areas of applicability of the present teachings will become apparent from the detailed description provided hereinafter. It should be understood that the detailed description and various embodiments, while indicating various embodiments, are intended for purposes of illustration only and are not intended to limit the scope of the teachings herein.

BRIEF DESCRIPTION OF THE DRAWINGS

The present invention will become more fully understood from the detailed description and the accompanying drawings, wherein.

DETAILED DESCRIPTION OF VARIOUS EMBODIMENTS

Although the following description and various examples may relate generally to a long bone procedure, such as a femur, it will be understood that the teachings herein may be applied to any appropriate procedure or implant. For example, the various elements may be combined to allow for an interconnection relative to a femur, such as interconnecting a bone replacing portion and a joint portion, or for interconnecting various portions of bony portions, such as the femur. Although modular systems may be provided for replacing a selected portion of a femur, it will be understood that various other prosthetic portions may be provided. For example, selected systems may be used to replace a selected portion of the tibia, the humerus, or other appropriate anatomical portions. Therefore, discussion of prosthetic portions or systems for replacement of selected body parts or anatomical portions will be understood to be merely exemplary and not intended to limit the teachings herein. Regardless, a system may be selected to interconnect various selected prosthetic systems, such as modular prosthetic systems, that may allow for customization for a selected patient by a user.

Various portions of the anatomy may be replaced or augmented with selected implants using a kit a presently described. For example, a joint replacement member may be implanted to replace a selected portion of a joint, such as a distal femoral prosthetic to replace the distal femoral articulation portion of the knee. Further, other portions or implants may be provided to interconnect the joint replacement portions with the bony portions or to interconnect the joint portion in an appropriate orientation. It will be understood that various other implant portions may be provided and they may also allow for soft tissue interconnection, joint reconstruction, joint stabilization, or other appropriate purposes.

Regardless, various types of implant portions are generally interconnected in selected manners. For example, various implant portions may be interconnected using taper, taper lock portions, threaded portions, etc. For example, a stem portion may be positioned in a selected portion of a bone member, such as an intramedullary canal, that extends to interconnect with a joint replacement portion. The stem member may include a selected portion of a taper, such as a male portion that may interconnect with a taper portion of the joint replacement portion. The male taper of the stem may be received to interconnect with a female taper that is defined by the joint replacement portion. This interconnection may generally hold the joint replacement portion relative to the stem after the implantation is complete and to fix the joint replacement portion in the selected anatomical location. Although general types of interconnections may be provided on various portions, the specifics of various interconnections may vary amongst different types of implant members. Regardless, it may be selected to interconnect various types of portions that may not have substantially matching interconnecting parts.

Therefore, a connector, according to various embodiments, may be selected from a kit to interconnect disparate or different connecting portions.

Figure 1A:
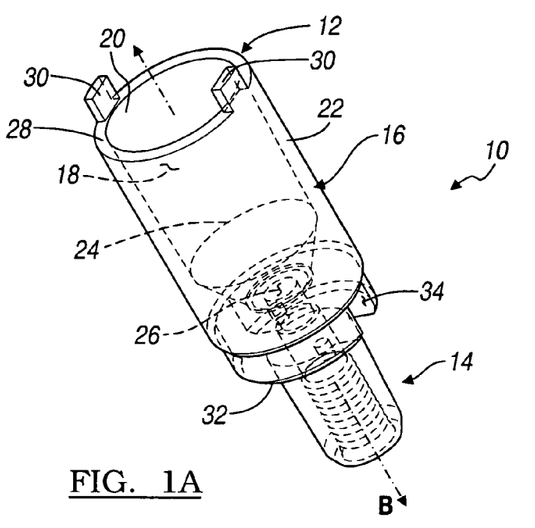
FIG. 1A is a perspective view of a connector usable with a kit according to first embodiment from a first end.
Figure 1B:
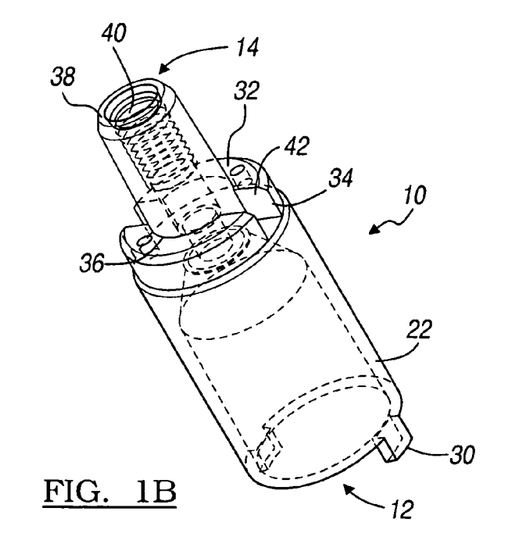
FIG. 1B is a perspective view of the connector FIG. 1A from a second angle.

With reference to FIG. 1A and FIG. 1B, a first connector 10 of a kit 400 (FIG. 8) may be used to interconnect different types of connecting portions, such as tapers. As described herein, the connector 10 is provided with the kit 400 that also includes a plurality of connectors including a connector 50, 80, and 120. The various connectors 10, 50, 80, 120, can be used in a selected manner to achieve a selected result, as discussed herein. The kit 400 can be provided to a user so that a user is able to select from the kit 400 a connector assembly for a particular situation or procedure.

The connector 10 generally includes a first end 12 and a second end 14. The first end 12 may be any appropriate end as may the second end 14. That being that the ends may be dependent upon the area of implantation or the portion of the connector 10 and how it interconnects with the other portions of the implant. The connector 10 may be used with any appropriate implant system and may be provided to interconnect a selected bone replacement portion or a stem and any other appropriate portion, such as a joint replacement portion. Nevertheless, depending upon the position, the orientation, and the type of system, the first end 12 may be a proximal or distal end, as may the second end 14. Therefore, it will be understood that the connector 10 may be implanted in any appropriate implantation system, position, or the like and the first and second ends 12, 14 respectively, may be dependent upon the specific location of the implantation.

Figure 1C:
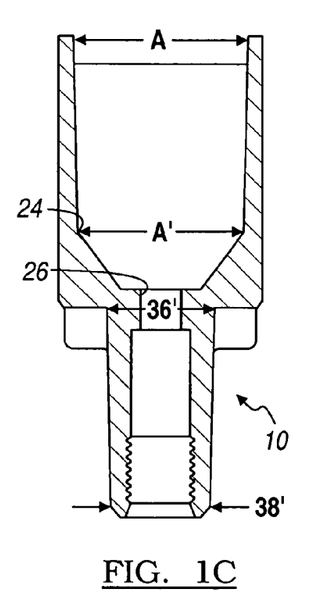
FIG. 1C is a cross-sectional view of the connector of FIG. 1A.

Near the first end 12, a taper defining portion 16 may be formed to define a female taper area 18. The taper defining portion may define a connection region type according to various embodiments. It will be understood that the taper portions, according to various embodiments, can define connection region types. An internal wall 20 and an external wall 22 may define the female taper area 18. The taper area 18 may include a diameter or dimension A that extends substantially perpendicular or across a longitudinal axis B of the connector 10. The longitudinal axis B may generally be aligned with other portions, such as discussed herein, to allow for positioning of the connector 10. The dimension A of the taper area 18 may be any appropriate dimension. Nevertheless, the dimension A of the taper 18 may be greater than a small dimension A' of the taper area 18. As discussed above, the taper area 18 generally defines a taper that tapers from the dimension A to the dimension A'. The taper area may terminate at a floor or base 24, which may define an opening 26 for various purposes.

The included angle from the floor 24 to the edge of the top portion 12 may include any appropriate included angle, such as about 1° to about 3°. The taper angle may allow for a locking or a substantially locking interconnection between the taper area 18 defined by the connector 10 or any appropriate portion interconnected therewith. It is understood that an included angle of about 1° to about 2° is generally a self-locking or anatomically acceptable taper connection. That is, two taper portions, such as a female taper portion and a male taper portion, can be self-locking if their included angles are about 1° to about 2° and form a connection that may not require a secondary or augmented locking portion. Therefore, the angle from A' to A may include an anatomically acceptable locking taper angle. Further, the dimension A may be any appropriate dimension such as about 20 mm to about 30 mm.

The upper area 12 may define a rim or stop portion 28. Extending from the rim 28 may be a tab or set of tabs 30. The tabs 30, as discussed further herein, may assist with interconnecting or holding the connector 10 relative to another portion or member. For example, the tabs 30 may interconnect with various portions of another portion to substantially resist or reduce rotation generally about the longitudinal axis B of the connector 10.

The upper area 12 may also define a lower bottom portion from which the lower end or second end 14 extends. Defined in a wall portion of the first end 12 is a depression 34. The depression 34 may interact with a portion, such as a tab similar to the tabs 30 on another member, for assisting and holding the connector 10 in a selected position. The depression 34 may interact with tab or other appropriate members to resist rotation of the connector 10 or for various other purposes.

The second end 14 generally includes an originating end or area 36 and an extending end or area 38. The extending area 38 may define a male taper adapted to be received in any appropriate member, such as a female taper. The extending area 38 may also define a connection region type, according to various embodiments, that can differ from the connection region type defined by the connector 10. For example, the second end 14 may define an external or male taper that has a major or larger diameter 36' at the originating end 36 and a smaller diameter 38' at the extending end 38. The angle of the taper defined by the second end 14 may be any appropriate taper angle that may allow for a selected interconnection. Further, in the second end, an engaging or locking portion 40 may be formed. The locking portion 40 may include internal threads that may engage a selecting locking member for various purposes, such as permanently interconnecting or fixedly interconnecting the connector 10 with a selected member. Further, the end 32 may define a stop area for engagement with a member, which is interconnected with the connector 10. Alternatively the portions may be designed to not touch such that the end 32 does not touch another portion. The end 32 may define a channel or depression 42 that may interconnect with another member for various reasons, such as reducing a rotation, reducing of other motions, or the like.

The taper of the second end 14 may generally be smaller than the taper defined by the taper area 18. It will be understood that the taper defined by the second end 14 may be any appropriate taper, which may be substantially different or similar to the taper defined by the first end 12. Nevertheless, the connector 10 may be used to interconnect various different portions, such that the taper defined by the first end 12 may be different than the taper defined by the second end 14 to allow for interconnecting of disparate or differing connecting portions. Therefore, the taper defined by the first end 12 may be larger than the taper defined by the second end 14. For example, the connector 10 may mate with a large male taper in the first end 12 and with a small female taper at the second end 14. For example, as discussed further herein, the connector 10 may interconnect with a small taper on a joint replacement member, while the larger taper defined at the first end 12 may interconnect with a large taper of a stem or bone replacement portion. Regardless, the various tapers may be used to interconnect differing portions or assemblies according to various embodiments.

Figure 2A:
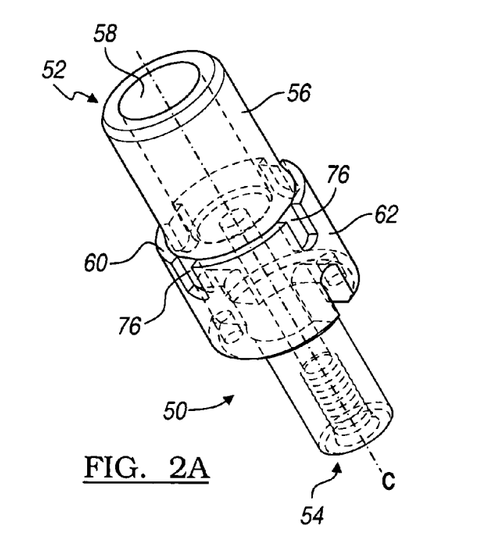
FIG. 2A is a perspective view from a first angle of a connector usable with a kit according to various embodiments.
Figure 2B:
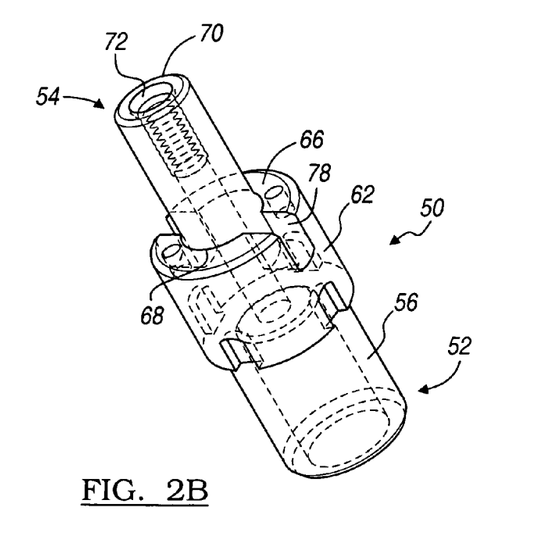
FIG. 2B is a perspective view of the connector FIG. 2A from a second angle.

With reference to FIG. 2A and FIG. 2B, a second connector 50 of the kit 400 may be provided including a first end 52 and a second end 54. The first end 52 may include an exterior wall 56 and an interior wall 58. The second end 52 may extend from a surface or a plateau 60 along a longitudinal axis C of the connector 50. A central region or portion 62 of the connector 50 may generally define the plateau surface 60.

The first end 52 may define a male taper defined by the external wall 56. As discussed above, the first end 52 can define a connection region type. The connection region type can be different than a connection region type defined by the second end 54 of the connector 50. The male taper may include a first diameter D near the plateau 60 and a second diameter D' near the end extending from the plateau 60. The taper may generally taper from the larger diameter D to the smaller diameter D'. The diameter D may have a dimension of about 20 mm to about 30 mm. Further, an included taper angle defined by the first end 52 may be about 1° to about 3°. As discussed above, the included angle of the first end 52 may mate with a female taper, such as the taper defined by the connector 10. Because the included angle range of about 1° to about 3° degrees substantially defines a self-locking or anatomically acceptable connection, a secondary connector may not be used.

The male taper defined by the first end 52 may be formed to interconnect with any appropriate portion, such as an articulating implant, a stem implant, or the like. Regardless, the male taper defined by the first end 52 may be formed to interconnect and/or hold the connector 50 relative to a first member while the second end 54 is operable to interconnect with a second member.

Figure 2C:
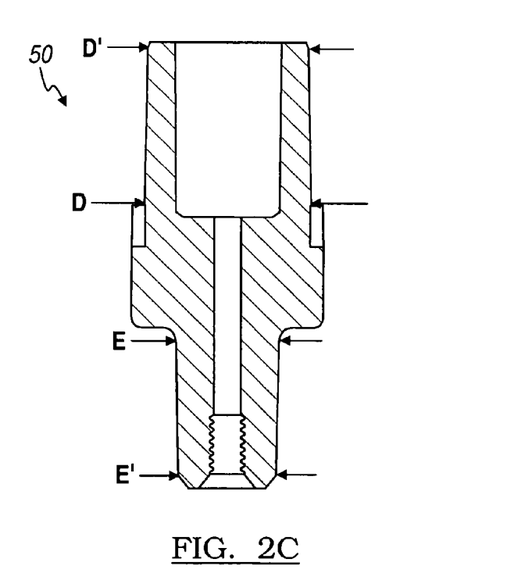
FIG. 2C is a cross-sectional view of the connector of FIG. 2A.

The central portion 62 may also define a second surface 66 from which the second end 54 may extend. The second end 54 may extend from an origin area 68 towards an extended area 70. The second end 54 may include a first diameter E, about 10 mm to about 20 mm, near the origin area 68 and a second diameter E' near the extended portion 70. Further, defined by the second end 54 may be an opened region or bore 72.

The diameters E, E' may define a taper defined by the second end 54. Therefore, the second end 54 may also define a male taper that extends from the second surface 66. The taper may include any appropriate included taper angle, such as about 2° to about 4°. Therefore, the taper defined by the second end 54 may form a substantially locking or fixing taper connection with a complimentary taper of a second member. The angle defined between E and E' may be an included angle of about 2° to about 4°. It will be understood that a female taper, such as the taper defined by the connector 80 between F and F' can substantially mate with the male taper defined by the second end 54 of the connector 50. The taper angle of about 2° to about 4° may be used with a secondary or augmented locking or connection portion to hold the two pieces together. Therefore, it may used with a secondary member to form an anatomically acceptable connection. It will be understood that an anatomically acceptable connection may be one that can be used in the anatomy and may either be the primary or only connection or may be a connection that includes a secondary connecting member.

The middle portion 62 may also define various regions, such as depressions 76 formed near the first end 52. Also, depressions or channels 78 may be formed near or on the second side 66 near the second end 54. The various channels or depressions 76, 78 may interconnect with various portions of other members, such as those discussed herein, to assist in holding the connector 50 relative to the other members. For example, various portions may extend into the channels or depressions to resist rotation or movement of the connector 50 relative to the other portions or the other portions relative to the connector 50. Therefore, the connector 50 may interconnect with other members with either the first end 52 or the second end 54 to be substantially held relative to various other members. The anti-motion or anti-rotation portion 76, 78 may assist in holding the connector 50 to the various members.

The first end 52 may engage a first type or first dimensioned female taper, while the second end 54 may engage a second type or second dimensioned female taper. Therefore, the connector 50 may be used to interconnect two different types of connection tapers to allow for an interconnection of disparate members. Further, it will be understood that the first end 52 and the taper defined thereby and the second end 54 and the taper defined thereby may be any appropriate tapers to interconnect with various portions. Also, various other members, such as locking screws, locking pins, etc. may be used to assist in fixing the connector 50 between two various portions. Therefore, the connector 50 may be used to permanently interconnect various portions or may be selectively disconnected to allow for other modifications.

Also, as discussed in relation to the connector 10, the first end 52 and the second end 54 may be any appropriate relative end. The connector 50 may be used in any appropriate interconnecting portion. Therefore, the first end 52 may be a substantially proximal or distal end, while the second end 54 may also be the other of the relative proximal or distal end. Therefore, it will be understood that the connector 50, including the first end 52 and the second end 54 may be interconnected with selected members of or in various combinations to achieve a selected result.

Figure 3A:
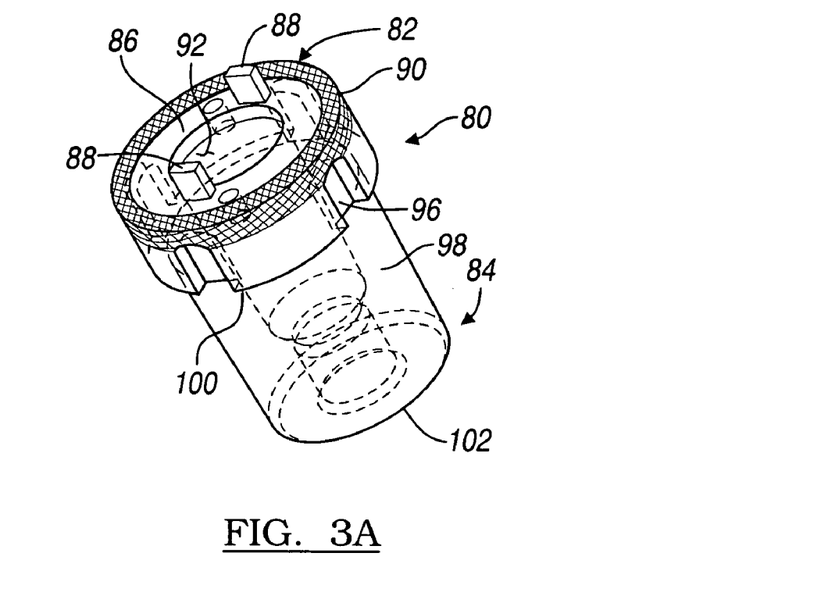
FIG. 3A is a perspective view of a connector usable with a kit according to various embodiments.
Figure 3B:
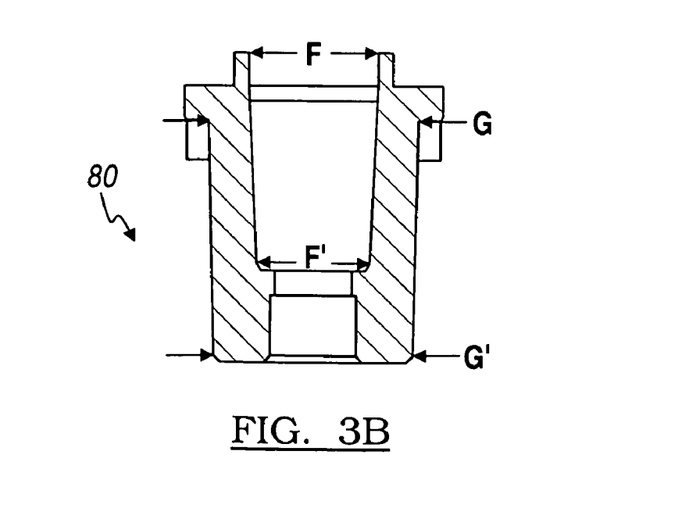
FIG. 3B is a cross-sectional view of the connector of FIG. 3A.

With reference to FIG. 3A and FIG. 3B, a third connector 80 of the kit 400 is illustrated. The connector 80 may also include a first end 82 and a second end 84. As discussed above, the first end 82 and the second end 84 may be any appropriate ends and formed relative to the connector 80 for various purposes. Therefore, the connector 80 may include the first end 82 as a proximal or distal end and a second end 84 as a proximal or distal end depending upon various applications of the connector 80.

The first end 82 generally includes an upper surface or rim 86 from which tabs or interconnecting portions 88 extend. One or more of the tabs 88 may extend from the rim 86 for various purposes. For example, the tabs 88 may engage various depressions or surfaces of other members to assist in holding the connector 80 relative to other appropriate members. The first end 82 may also include a porous coated region to assist in interconnecting the connector 80 with a selected member. Further, the rim region 90 may assist in bony ingrowth if selected.

Also, defined by the first end 82 is a bore 92 that may define a taper. The bore 92 may define a female taper including a first diameter F near an exterior and a second diameter F' near an interior of the bore 92. The bore 92 can define a connection region type that can be different than a connection region type, as discussed herein, defined by the second end 84. The bore 92 may define a female taper that includes an included selected taper angle of about 2° to about 4°. Therefore, the female taper 92 may interconnect with a male taper of a complimentary taper angle to allow for a holding or substantially fixed connection of the connector 80 to another member.

The first end 82 may also define a depression or recess 96 that may be engaged by or engage other portions, similar to the tabs 88 to assist in holding the connector 80 in a selected position. The depressions 96 may assist in holding other various members in a substantially fixed or non-rotational orientation relative to the connector 80.

The second end 84 generally includes an external wall 98 that extends from a surface 100 from the first end 82. The wall 98 may define a male taper that extends from the surface 100 to an end 102 of the second end 84. The male taper may include a large diameter G and a small diameter G'. Therefore, the male taper 98 may include an included taper angle of about 1° to about 3°. This may allow the male taper 98 defined by the second end 84 to interconnect with a selected female taper. The taper angle of the male taper 98 may be formed to be interconnected in a substantially fixed manner or in a manner that is augmented with a second member, such as a screw or pin, to insure a fixed connection. Regardless, the male taper 98 may interconnect with a selected member to assist in holding the connector 80 relative to the other member.

Further, the female taper 92 defined by the connector 80 may engage a male taper of a selected dimension, while the male taper defined by the second end 84 may engage a female taper of a second dimension. Therefore, as discussed above, the connector 80 may be used to interconnect different taper sizes or different prosthesis systems. For example, the female taper 92 may engage a male taper that is smaller than the male taper defined by the second end 84, while the female taper defined by the second end 84 may be larger than the female taper 92. Therefore, different systems may be interconnected and used together with the connector 80 that may not otherwise be possible.

Figure 4A:
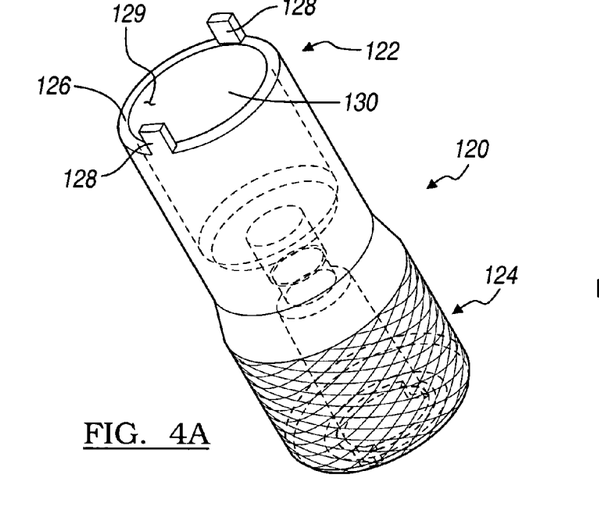
FIG. 4A is a perspective view from a first angle of a connector usable with a kit according to various embodiments.
Figure 4B:
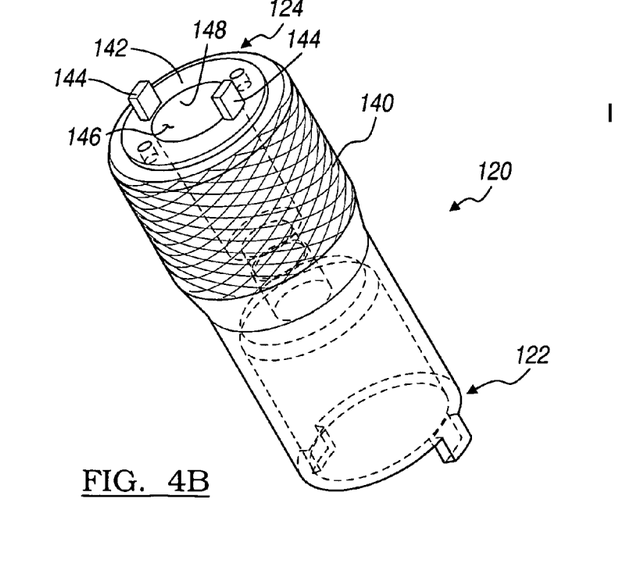
FIG. 4B is a perspective view of the connector of FIG. 4A from a second angle.
Figure 4C:
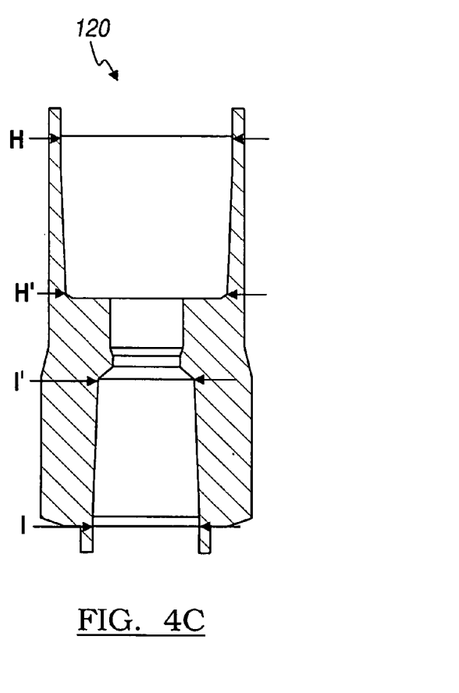
FIG. 4C is a cross-sectional view of the connector of FIG. 4A.

With reference to FIGS. 4A-4C, a fourth connector 120 of the kit 400 is illustrated. The connector 120 includes a first end 122 and a second end 124. The first end 122 generally includes an upper ridge or surface 126. Extending from the upper surface 126 is a tab or projection 128. The tab 128 may include a plurality of tabs according to various embodiments. Further, the first end 122 defines a bore or wall 129. The bore 129 may be formed in the first end 122 for various purposes.

For example, the bore 129 may include a first dimension or diameter H that tapers to a second dimension H' within the first end 122. The bore 129, briefly, can define a connection region type that is different than a connection region type defined by the second end 124 of the connector 120. The wall 130 that defines the bore 120 generally defines a taper angle that diminishes from the first end or surface 126 to the minimum diameter that defines H'. Therefore, the wall 130 may define a female taper, including an included taper angle of about 1° to about 3°. The second end 124 may include an exterior surface or portion 140 that has roughened or porous coat for various purposes. For example, the roughened surface 140 may assist interconnecting the connector 120 with various portions or may be substantially coated or formed to allow for bony ingrowth or adhesion. Further, the second end 124 includes an exterior surface 142 from which a tab or member 144 may extend. It will be understood that a plurality of the tabs 144 may be provided for various purposes.

Defined through the first end 142 is a bore 146 that is defined by an anterior wall 148. The anterior wall 148 and the bore 146 may define an end or top diameter I of a selected dimension and an internal or smaller I' of a second dimension. The difference in dimensions between I and I' define a taper defined by the wall 148. The taper defined by the wall 148 may be any appropriate taper and may include an included taper angle of about 2° to about 5°. Therefore, the taper defined by the anterior wall 148 may interconnect with a selected male taper for various purposes.

The connector 120, including the female taper defined by the wall 148 and the female taper defined by the wall 129, allows for interconnection with a male taper. The taper angle or dimensions of the taper wall 129 may differ from the taper angle or dimensions defined by the wall 148. Therefore, the male taper, that interconnects with the first end 122, may be different than a male taper that may interconnect with the second end 124. Therefore, the member 120 may be used to interconnect the various different male tapers, such as those that may be used by different systems. Regardless, the connector 120 may be used to interconnect and be held relative to various male tapers for various purposes, such as interconnecting particular members of a system or providing an extension therefore. Further, it will be understood that the tapers defined by the first end 122 and the second end 124 may be substantially self locking tapers or may be used with other members, such as screws, locking pins, and the like to lock or hold the connector 120 relative to a selected position. Nevertheless, the connector 120 may be used to interconnect different sized male tapers to allow for interconnection of various systems that are different from one another, such as those discussed above and herein.

Figure 5:
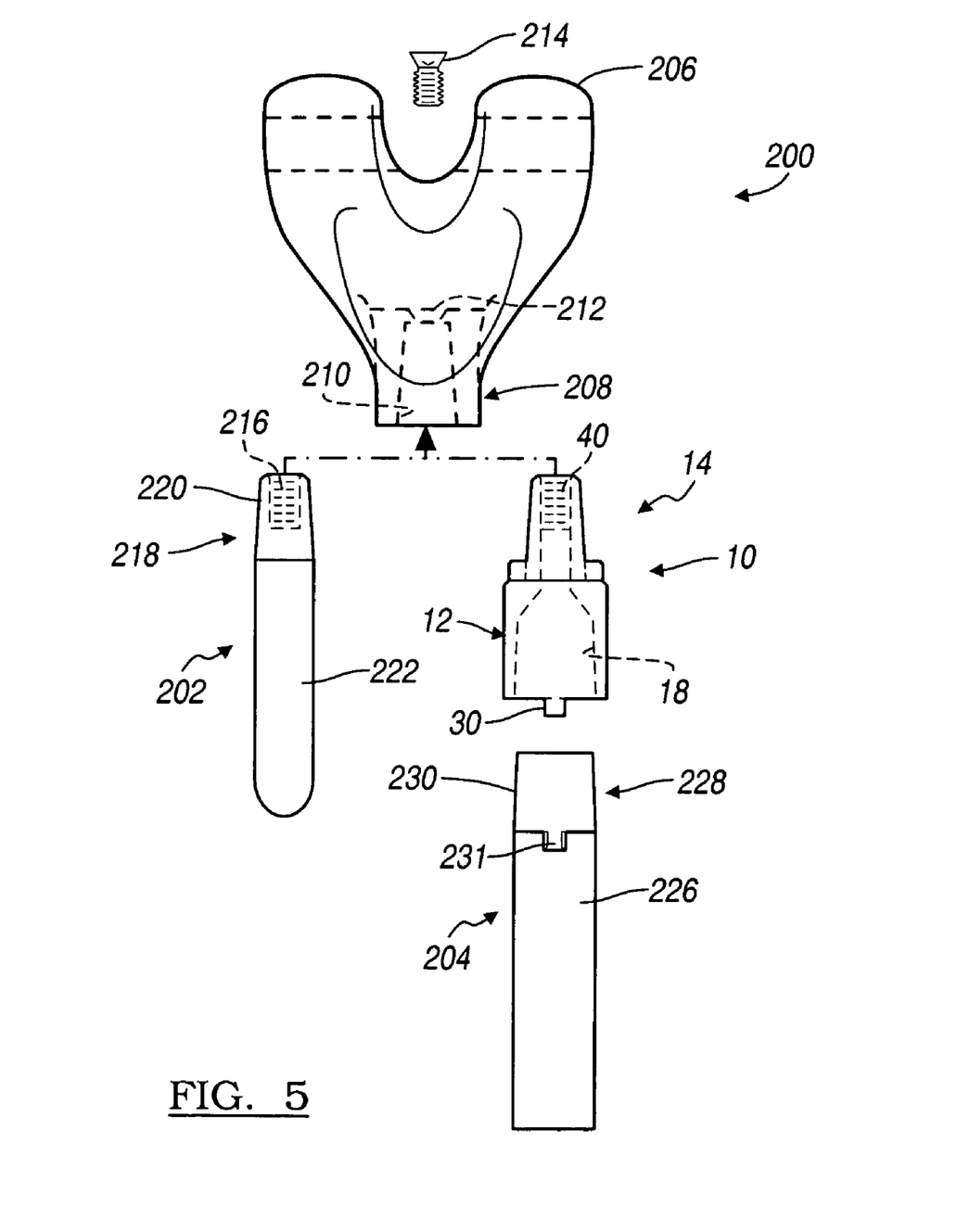
FIG. 5 is an exploded view of an implant assembly according to selected embodiments.

An implant assembly 199, as illustrated in FIG. 5, may include an articulation or a joint replacement portion 200. A stem portion 202 or an alternative stem portion 204 that may be used with the connector 10. The implant assembly 199 may be a modular assembly where the articulation portion 200 is separate from the stem 202. Regardless, the assembly 199 may be used together to replace a selected portion of the anatomy. For example, the articulation portion 200 may be used to replace a distal femoral portion, such as replacing the condyles of the femur in the knee. Nevertheless, it will be understood that the joint replacement portion 200 may be any appropriate portion such as a proximal femoral portion, a humeral portion, or any appropriate portion. The articulation portion 200 may be separate from the stem portion 202 for various reasons, such as ease of implantation, selection and customization by a user, such as a surgeon, or other appropriate reasons.

The articulation portion 200 may include an articulation region 206. The articulation region 206 may be any appropriate articulation region, such as a replacement for a condyle in the femur. The articulation region 206 may, however, be any appropriate articulation region, such as replacing a femoral head of the femur, a humeral head of a humerus, or any appropriate portion. Nevertheless, the articulation region 206 may be adapted to articulate with a selected portion of the anatomy, a second articulation implant, or any appropriate member.

The articulation component 200 can further include an interconnection or connection portion 208. The connection portion 208 may be any appropriate connection portion and may include or define an internal taper 210. The internal taper 210 may be any appropriate taper, such as including an included taper angle of about 2° to about 5°. Further, the connection portion 208 may include a locking portion or member, such as a screw hole 212. A screw 214 may be provided through the screw hole 212 to substantially lock or interconnect in a selected manner with a component, such as the stem 202. The stem 202 may include an internally threaded portion 216 that is operable to receive or interact with the screw 214. Regardless, it will be understood that any appropriate portion may be used to hold together the articulation component 200 and the stem 202. Such systems include the OSS™ system sold by Biomet, Inc. of Warsaw, Ind.

The stem 202 includes a connection region or portion 218 that may define or include the internal threads 216. Further, a taper 220 may be defined by the connection region 218. The external taper 220 may be formed to substantially mate or lockably interconnect with the internal taper 210. For example, a Morse taper may be used to fixedly interconnect the stem 202 with the articulation member 200. The stem 202 also includes a bone engaging or intramedullary portion 222. The intramedullary portion 222 may be positioned in any appropriate bone member. For example, as illustrated in FIG. 5, the articulation member 200 may be a distal femoral articulation portion and replace a portion of the knee. Therefore, the stem 200 may be adapted or formed to be positioned in the intramedullary canal of the femur to hold the articulation portion 200 in a selected position. The connection portion 218 may be used to interconnect with the articulation portion 200 to hold the articulation portion 200 to articulate the tibia or a tibial implant.

The stem portion 204 may be a second or alternative bone engaging portion. The stem 204 may include a bone engaging or intramedullary portion 226. Alternatively, the bone engaging portion 226 may be adapted to substantially replace portions of bone. For example, the portion of bone to which the stem 204 may be interconnected may be diseased or otherwise compromised. Therefore, the bone engaging portion 226 may include a diameter substantially larger than a diameter of the bone engaging portion 222. Therefore, the second stem 204 may be used for various reasons, other than only attaching the articulating portion 200 to a selected bone portion.

Regardless, the second stem portion 204 may also include an engaging portion 228. The engaging portion 228 may include a taper 230 of a selected type, such as one including an included taper angle of about 2° to about 5°. The second taper may be similar to the taper used in the Compress™ system sold by Biomet, Inc. of Warsaw, Ind. The taper 230 that does not need a second locking or connecting member may be viewed as providing an anatomically acceptable connection with the taper connection alone. Though it will be understood that other connections alone may also be sufficient. The taper 230 defined by the second stem member 204 may include a taper that is differently sized and/or not otherwise matable with the internal taper 210 defined by the articulating portion 200. Therefore, the connector 10 may be provided to allow for interconnection of the second stem 204 to the articulating portion 200. As discussed above, the connector 10 may include a male taper or second end 14 operable to interconnect with the internal taper 210 of the articulation member 200 and may define a female taper 218 to interconnect with the connection portion 230. Thus, the second stem member 204 may be interconnected with the articulation member 200 for use in various procedures.

It will be understood that the connector member 10 may be used for any appropriate purpose and may include various different connection sizes. For example, the second end 14 may include a larger taper size than the first end 12. Or, in the alternative, the first end 12 may include a smaller taper than the second end 14. Regardless, the connector 10 may be provided to interconnect various disproportionately sized taper or connection portions. Further, the first end 14 may include internal threads in the bore 40 defined in the connector 10. This may allow it to interconnect with the articulation member 200 in a selected manner.

The second stem member 204 and the connector 10 may be used together for other various reasons as well. For example, the articulation member 200 may be substantially permanently connected to an implant assembly, such that it's removal is undesirable or difficult. Therefore, it may be desired or selected to maintain the articulation member 200 in the implanted position, but still use the second member 204. Therefore, the connector 10 may be used to interconnect with the articulation member 200 in selected circumstances. Therefore, if the articulation member 200 is already positioned and the second stem member 204 is selected, it may be interconnected with the articulation member 200 without removing the articulation member 200 even if the articulation member 200 is not directly interconnectable with the second stem member 204. Therefore, it will be understood that the connector 10 may be used in any appropriate procedure, such as replacement of the stem 204, a procedure to resect a selected portion of the bone to position the second stem therein, or any appropriate reason.

Figure 6:
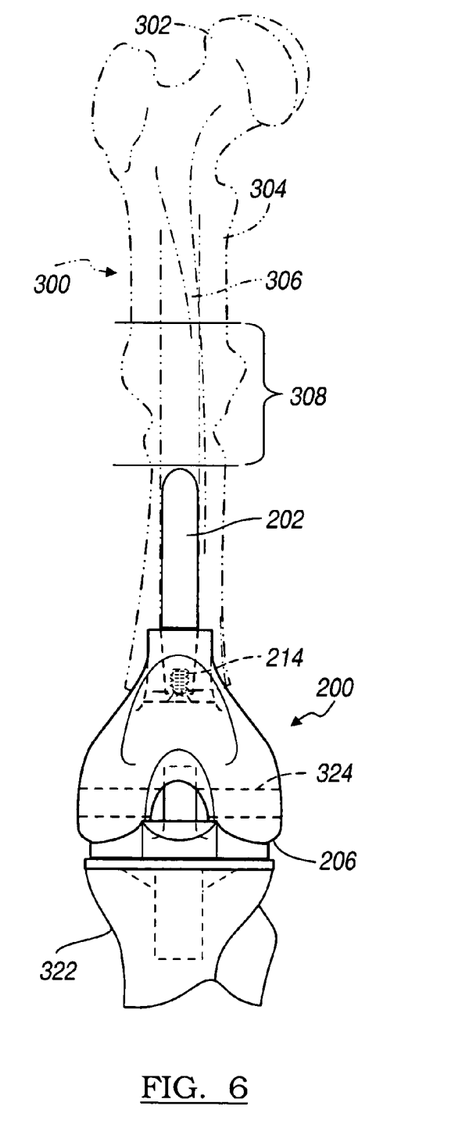
FIG. 6 is an environmental view of an implant assembly usable with a kit according to various embodiments.
Figure 7:
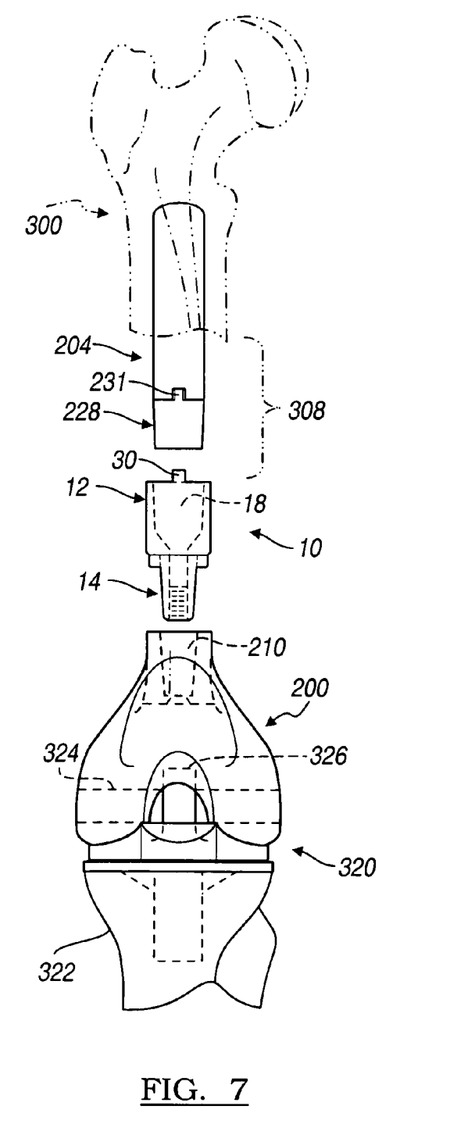
FIG. 7 is an exploded environmental view of an implant assembly according to various embodiments.

With reference to FIG. 6 and FIG. 7, the implant assembly may be provided in a bone portion 300 for various purposes. For example, the bone portion 300 may be a femur that includes a femoral head 302, a shaft portion 304 that includes an intramedullary portion 306, and a diseased or compromised portion 308. The assembly, including the articulation portion 200 and the first shaft 202 may be positioned in the bone 300 for various purposes, such as replacing the distal articulating portion. Therefore, it will be understood that the implant assembly may be implanted in various pieces and interconnected in a selected procedure. For example, the articulating member 200 may be interconnected with the stem member 202 in a first procedure and implanted into the bone 300. At a later time, the bone 300 may develop the injurious portion 308 for various reasons, such as disease, cancer, injury, or the like. Regardless, the stem member 202 may no longer provide satisfactory interconnection between articulation member 200 and the bone 300. This may be because the injurious portion 308 may be between the stem member 202 and a healthy portion of the bone 300 or because the stem member 202 extends through the injurious portion 308. Regardless, it may be selected to replace the stem member 202.

As illustrated in particular in FIG. 7, the first stem member 202 may be replaced with the second stem member 204. The bone portion 300 may be resected an appropriate amount to remove the diseased or injurious portion 308. The second stem member 204 may be provided through the bone member 300. Further, a substantial portion of the intramedullary canal 306 may be removed when the second stem 204 is provided. Therefore, the second stem member 204 may not be substantially held within the intramedullary canal of the bone 300, but may be held in a cancellous portion of the bone 300. Regardless, the articulation member 200 may be maintained in the patient for various purposes.

The connector 10 may be used to interconnect the second stem member 204 with the articulation member 200. As illustrated in FIG. 5, the connector 10 may include a second end 14 to interconnect with the female taper 200 defined by the articulation member and the first end 12 defining the taper 18 to interconnect with the connection portion 228 of the second stem 204. Also, the tabs 30 of the connector 10 may operably engage depressions 231 in the second stem 204. This engagement or connection may assist in steadying the connector 10 relative to the second stem 204. Therefore, the articulation member 200 may be maintained in the patient for various purposes.

For example, the articulation member 200 may be substantially fixedly interconnected with a tibial member 320. The tibial member 320 may be fixed within a tibia 322 for replacing articulation portion of the tibia 322. Extending through the articulation member 200 and an intercondylar portion 326 may be an axle or hinge portion 324 that interconnects with a portion of the tibial member 320. The intercondylar portion 326 may be fixed or hingedly connected to the articulation member 200 for various purposes, such as providing a connection between the tibia portion 320 and the articulation member 200. It may be selected to maintain the connection for various reasons such as the hinge connection is still required or the articulation portions are still operable for other purposes. Therefore, the connector 10 may be used to interconnect the second stem member 204 with the articulation member 200 with only the portions of the implant other than the articulation member 200 need to be replaced. As discussed above, various reasons may be required for replacing the first stem member 202, such as further injury to the bone 300, further disease to the bone 300, or various other reasons.

Further, the connectors, according to various embodiments, may be used in other portions of the anatomy for reasons other than articular portions. For example, with exemplary reference to FIG. 6, the bone 300 may include the injurious portion 308, but no implant portions. Nevertheless, the injurious portion 308 of the bone 300 may need to be replaced. For various reasons, it may be desirable to provide an implant of the bone 300 that is operable to remove or replace the injurious portion 308 while maintaining the articulation portion, such as the head 302 and the distal articulation portion of the bone 300. It may be difficult to interconnect various systems of implants or it may be selected to use different implant systems to interconnect or replace the injurious portion 308 of the bone 300.

For example, various connecting or connection types may require the use of a second or locking portion to firmly hold the implant members together. Other connecting types, however, may not require a second or additional locking member. Such taper locking systems include the Compression™ system by Biomet, Inc. Therefore, a first member may be connected or positioned in the bone 300 of a first implant type. The connector 10 may then be provided and locked in place with a locking screw or other locking member. A second member of a second implant system may be positioned in a second portion of the bone and connected with the connector 10 with no further locking or secondary locking portion. Therefore, the injurious portion of the bone 308 may be replaced with an implant assembly while maintaining the articulation portions of the bone member 300. It will be understood, however, that the connector 10, or connector according to any appropriate embodiment, may be used for various purposes. The adaptor may replace a stem member connected in the anatomy, allow for an interconnection between disparate implant types or connection portions, or any other appropriate reasons. Further, although the examples provided above relate generally to replacing various portions of a femur, it will be understood that any appropriate implant may be implanted at any appropriate bone member, such as in a humerus, a tibia, or other portion.

Figure 8:
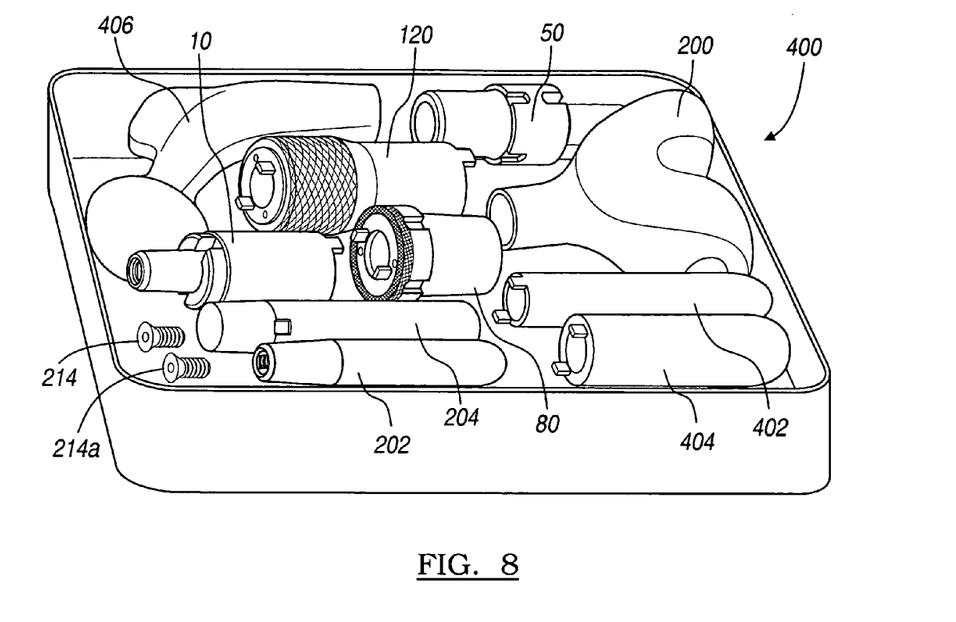
FIG. 8 is a perspective view of the kit including various components according to various embodiments.

With reference to FIG. 8 an implant system may be provided including at least the connectors 10, 50, 80, and 120 as discussed above according to various embodiments. As discussed above the connectors may define locking portions, such as tapers, that when mated or interconnected with selected portions, create a connection that is anatomically acceptable. Generally, the taper portions 18, 56, 98, and 129 define anatomically acceptable taper locks. It will be understood that the other connection portions may allow a connection between various portions that it may be selected to provide a secondary locking element, such as a screw, to form an anatomically acceptable connection.

The kit 400 may also include other parts or members such as intercalary stems 402 and 404. Moreover, the kit 400 may include the implant articulation member 200 and a proximal femoral implant member 406. The articular parts may be of any appropriate configuration, such as those generally known in the art. Moreover, the articulation member may be a modular system that is interconnected during an operative procedure, such as a femoral head of the proximal femoral implant member 406 may be modular.

The kit 400 may be provided for a selected procedure or portions therefrom may be selected prior to a procedure. For example, with reference to FIG. 9 an intercalary implant system 401 may be provided. The intercalary system 401 may include the connector 50 and the connector 80. The two connectors 50, 80 may be provided between a first stem member 404 and a second stem member 406. The stem members 404, 406 may be provided in a selected bone member for various purposes. For example, as illustrated in FIG. 6, a diseased portion 308 of the bone 300 may exist. The diseased portion may need to be removed or repaired, even if an articulation member, such as a distal femoral portion 200, is not provided.

Figure 9:
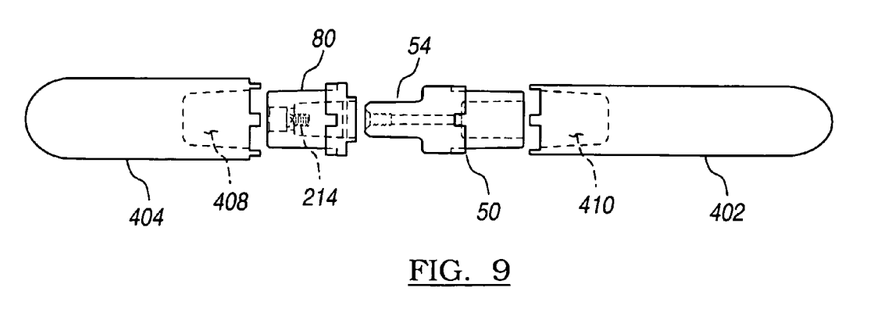
FIG. 9 is an exploded view of an implant assembly usable with a kit according to various embodiments.

Thus the bone 300, or any appropriate bone portion, may be prepared by removing the diseased portion 308. The first stem member 402 may then be positioned in the bone 300 as may the second stem member 404. A connector assembly including the connectors 50 and 80 may then be provided. The two connectors 50, 80 may be connected in any appropriate manner, such as with a taper connection. The male taper portion of the second end 54 of the connector 50 may be positioned relative to the female taper 92 of the connector 80. As discussed above a locking or secondary member, such as the screw 214, may be provided to create an anatomically acceptable connection. The assembled connectors may then be positioned in a first of the stems member 402 and 404 and then the other of the stem members 402 or 404. Alternatively, one of the connectors 50, 80 may be positioned in the stem member 402 and then the locking member 214 may be positioned to provided the anatomically acceptable connection.

Regardless of the order, the second end 84 of the connector 80 may be positioned in the female taper 408 defined by the second stem member 404. Similarly, the first end 52 of the connector 50 may be positioned in the female taper 410 of the stem member 402. The taper 56 of the connector 50 and the taper 98 of the connector 80 may interact with the respective female tapers 410, 408 of the stem member 402, 404 to form an anatomically acceptable connection with no other members. Thus, the two stems 402, 404 may be implanted as an intercalary implant because they can be forced together, such as a with a blow or compressing device, to form the anatomically acceptable connection. The tapers may define the appropriate taper angles, such as those discussed above and such as those generally used in the Compress™ system sold by Biomet, Inc. of Warsaw, Ind.

Other various connections will be understood to be possible. The various connectors 10, 50, 80, and 120 can be provided in any appropriate combination to form a selected implant or connector assembly. The various connectors may be provided to form connections that are anatomically acceptable, such as those described above, to interconnect various implant systems, and other appropriate purposes. Thus the purposes described herein are merely exemplary and not intended to limit the teachings herein.

Figure 10A:
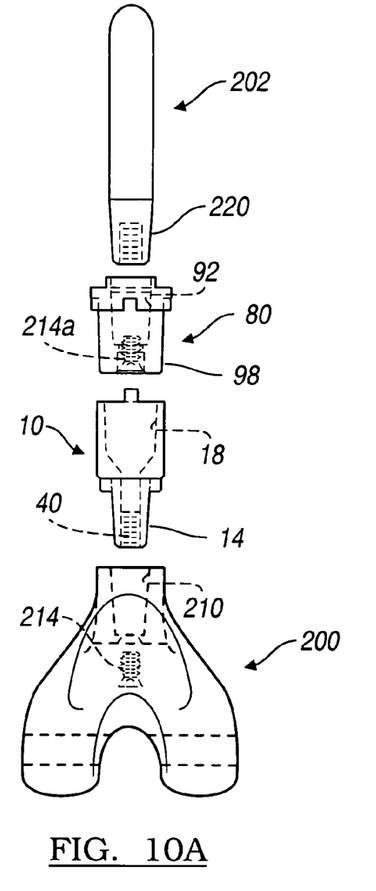
FIG. 10A is an exploded view of an implant assembly usable with a kit according to various embodiments.
Figure 10B:
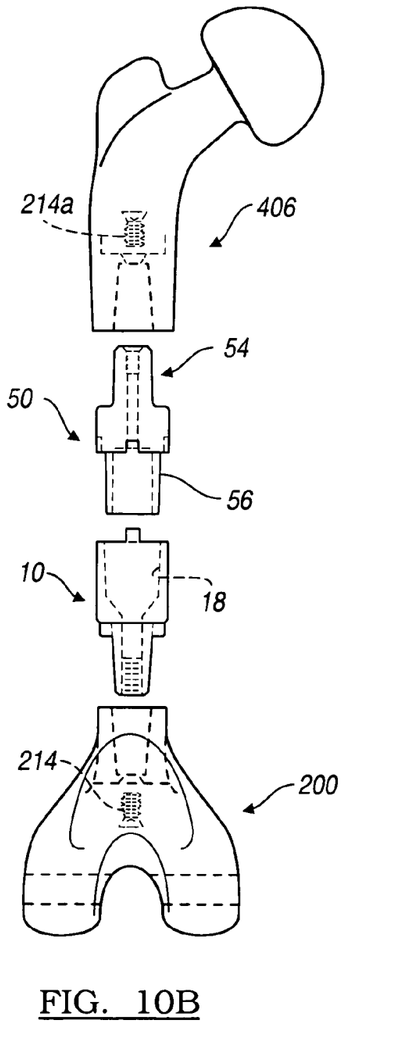
FIG. 10B is an exploded view of an augmented implant assembly usable with a kit according to various embodiments.

With reference to FIGS. 10A and 10B, an implant system may be formed from the elements included in the kit 400. Further, the system may be used for various reasons, such as a revision or supplementary procedure. Therefore, a first portion of the procedure may occur at a first time and a second portion of the procedure may occur at a second time. Further, with reference to FIGS. 10A and 10B, two different possibilities may exist for a procedure that may be formed from the components of the kit 400. Therefore, a selection may be performed intraoperatively, if necessary, depending upon the patient from the components of the kit 400.

With initial reference to FIG. 10A, the articulation component 200 may be a distal femoral articulation component. The distal femoral articulation component may be any appropriate distal articulation femoral component as is generally known in the art. The distal femoral articulation component may be similar to the component illustrated in FIG. 7 above. The distal articulation component 200 may include the taper or connection portion 210. A screw 214 may be provided through the implant member 200 to engage a thread 40 in the connector 10. The connector 10 may also include the second end 14 that is operable to engage the taper 210. Therefore, the articulation member 200 can be anatomically fixed to the connector 10. The screw 214 may be used for various purposes such as allowing for a substantially anatomically acceptable connection between the articulation number 200 and the connector 10.

The assembly of the connector 10 and the implant member 200 may be further interconnected with a second connector such as the connector 80. The connector 80 may be received within the internal taper 18 of the connector 10 by interconnecting the male taper 98 therewith. The second connector 80 may allow for interconnection with the stem 202 by engaging or interconnecting the male taper 220 of the stem 202 with the female taper 92 of the connector 80. Therefore, the implant assembly that may include the stem 202, the connector 80, the connector 10, and the implant member 200 may be provided into a selected portion of the anatomy.

The assembly may be implanted into a distal portion of the femur similar to that illustrated in FIG. 6. This may be performed at an initial procedure to replace the distal femoral portion. Nevertheless, the kit 400 may be used to provide the various connectors to interconnect the various portions of the implant. Further, as discussed above, a secondary member, such as a second screw 214a, may be provided to form an anatomically acceptable interconnection between the stem 202 and the connector 80. Nevertheless, the male taper 98 defined by the connector and the female taper 18 defined by the connector 10 may form a substantially anatomically acceptable interconnection with no further or secondary connection members. Therefore, the connectors 80, 10 may be used to position or hold the implant member 200 relative to a selected portion of the anatomy, such as near a knee of the anatomy.

With reference to FIG. 10B, the implant member 200 may be interconnected as illustrated in FIG. 10A. That is, the distal femoral portion 200 may be interconnected with the connector 10 which may include the interconnection of the secondary locking member 214. This portion may be substantially positioned near the knee in a patient such as a distal femoral portion. Nevertheless, for various reasons, the proximal portion including the stem 202 may need to be replaced or augmented for various reasons. For example, a proximal implant 406 may be necessary in a selected patient. Therefore, because of the various connectors, the proximal femoral component 406 may be interconnected with the connector 10 and the distal femoral component 200 without requiring access to the knee portion of the anatomy to remove the screw member 214.

The female taper 18 may be disengaged from the connector 80 as originally implanted, as illustrated in FIG. 10A. The female taper 18 may then be interconnected with an implant member, such as the connector 50. The connector 50 may define the male taper portion 56 that can form an anatomically acceptable interconnection with the connector 10. No secondary locking member may be necessary to interconnect the connector 50 and the connector 10. Nevertheless, the proximal femoral component 406 may be interconnected with the connector 50 by engaging the second end 54 of the connector 50 in a taper 450 defined by the proximal femoral components. The second secondary locking member 214a may be provided to interconnect the proximal femoral component 406 with the connector 50 to provide for an anatomically acceptable interconnection between the connector 50 and the proximal femoral component 406.

The assembly of the connector 50 and the proximal femoral component 406 may be interconnected with the connector 10 and the distal femoral component 200 with no secondary connection member due to the interaction of the male taper 56 and the female taper 18. Therefore, the originally implanted distal femoral component including the distal femoral member 200 may be formed into a second implant assembly including the proximal femoral component 406 without requiring access to the knee portion of the anatomy. This may provide a substantially reduced procedure for an individual and provide for a faster healing and return to activity of the individual. The various components of the kit 400 may provide for the procedure by allowing for an interconnection or a selected interconnection of various components that may include or may not include secondary locking members. Regardless, it will be understood that the kit 400 may provide for a connection of various component members that may be selected by a user, such as a surgeon, for various procedures.

It will be further understood that other combinations or uses of the kit 400 are within the teachings of the present disclosure. For example, with exemplary reference to FIGS. 6, 7, 10A, and 10B, the implant system, the parts of the kit 400, may be used to achieve an augmented or changed implant system without necessarily disconnecting or obtaining access to a joint region. For example, with reference to FIG. 7, the implantation of the distal femoral component 200 in conjunction with the tibia component 320 in a knee may require the manipulation of several soft tissue portions. However, the replacement of the stem portion 204 in the other portion of the bone 300 may also be performed during a primary or initial procedure. Nevertheless, during a revision procedure the stem 204 may be removed from the connector 10 without obtaining access to the knee region which includes the components 200 and 320. Therefore, the revision procedure can occur where either more bone from the bone 300 is removed, a longer stem is used to replace the stem 204, or any other appropriate procedure occurs without getting access to the joint region. For example, as illustrated in the FIGS. 10A and 10B, the distal femoral component 200 can be implanted and interconnected with the stem 202 using various connectors 10, 80. The procedure that may occur to replace the stem 202 and interconnect a proximal femoral component 406 can occur without obtaining access to the knee region or the distal femoral component 200. Rather the stem 202 can be removed and the connector 80 replaced with the connector 50 to allow for interconnection of the proximal femoral component 406 with the distal femoral component 200.

Therefore it will be understood that the various connectors and the implant system of the kit 400 can be used to perform procedures without requiring access to various portions of the anatomy. In other words, the kit 400 allows for augmentation, replacement of various components, or other procedures without requiring access to an entire portion of the patient's anatomy. As discussed above, various procedures may occur relative to portions of the femur without requiring access to joint portions or other portions. Regardless that new components are going to be interconnected with the previously implanted or already positioned components, access thereto may not be necessary.

Further, it will be understood that the connectors, as discussed above, need not be limited to taper connections. The connections may include threads, locking rings or members, or other appropriate connections. Thus, the above discussion regarding tapers is not intended to limit the scope of the present teachings.

The teachings herein are merely exemplary in nature and, thus, variations that do not depart from the gist thereof are intended to be within the scope of the teachings. Such variations are not to be regarded as a departure from the spirit and scope of the teachings.

What is claimed is:

1. A modular implant system for being positioned in an anatomy, comprising:
a first implant member having an articulating portion and operable to be positioned in the anatomy;
a second implant member operable to be positioned in the anatomy;
a third implant member having an articulating portion and operable to be positioned in the anatomy;
at least three connectors including a first, a second and a third connector, wherein each of the three connectors include a first end and a second end; and
at least two of the connectors are interconnectable to form a connector assembly, wherein in a first configuration, the first and second connectors are interconnected between the first and second implant members and in a second configuration, the first and third connectors are interconnected between the first and third implant members;
wherein the first ends of the second and third connectors include the same connection region type while the second ends of the second and third connectors include distinct connection region types, wherein both of the first and second ends of the third connector are one of male or female insertion portions and one of the first and second ends of the third connector is larger than the other of the first and second ends of the second connector, wherein the larger one of the first and second ends includes a larger diameter taper connection.

2. The modular implant system of claim 1, wherein the second implant member includes a stem operable to be positioned in the intramedullary canal of a bony structure.

3. The modular implant system of claim 2 wherein in the second configuration, the articulating portions of the first and third implant members provide articulating portions of a femoral knee implant and a femoral hip stem, respectively.

4. The modular implant system of claim 1 wherein the same connection region type includes one of male insertion portions or female receiving portions.

5. The modular implant system of claim 1 wherein the same connection region type includes tapering surfaces of identical geometries.

6. The modular implant system of claim 1 wherein the second connector and the second implant member are operable to be replaced from the first configuration with the third connector and the third implant member in the second configuration in a revision procedure while the first connector and the first implant member are left in an implanted position.

7. The modular implant system of claim 1 wherein in the first configuration, the first end of the second connector is directly attached to a first end of the first connector and the second end of the second connector is directly attached to the second implant member, and wherein a second end of the first connector is directly attached to the first implant member.

8. The modular implant system of claim 7 wherein in the second configuration, the first end of the third connector is directly attached to the first end of the first connector and the second end of the third connector is directly attached to the third implant member, and wherein the second end of the first connector is directly attached to the first implant member.

9. The modular implant system of claim 1, further comprising a fourth connector having a first and a second end that are both one of male insertion portions or female receiving portions.

10. The modular implant system of claim 9 wherein one of the first and second ends of the fourth connector is larger than the other of the first and second ends of the fourth connector.

11. A modular implant system for being positioned in an anatomy, comprising:
a femoral knee prosthesis having an articulating portion and operable to be positioned at a distal femur in the anatomy;
a second implant member operable to be positioned in the anatomy;
a femoral hip stem having an articulating portion and operable to be positioned at a proximal end of the femur in the anatomy;
at least three connectors including a first, a second and a third connector, wherein each of the three connectors include a first end and a second end; and
at least two of the connectors are interconnectable to form a connector assembly, wherein in a first configuration, the first and second connectors are interconnected between the femoral knee prosthesis and the second implant member and in a second configuration, the first and third connectors are interconnected between the femoral knee prosthesis and the femoral hip stem;
wherein both of the first ends of the second and third connectors include a male tapered insertion portion or a female tapered receiving portion while the second ends of the second and third connectors include distinct connection region types, wherein both of the first and second ends of the third connector are one of male insertion portions or female receiving portions and one of the first and second ends of the third connector is larger than the other of the first and second ends of the second connector, wherein the larger one of the first and second ends includes a larger diameter taper, and wherein both of the first ends of the second and third connectors includes tapering surfaces of identical geometries.

12. The modular implant system of claim 11, wherein the second implant member includes a stem operable to be positioned in the intramedullary canal of a bony structure.

13. The modular implant system of claim 11 wherein the second connector and the second implant member are operable to be replaced from the first configuration with the third connector and the femoral hip stem in the second configuration in a revision procedure while the first connector and the femoral knee prosthesis are left in an implanted position.

14. The modular implant system of claim 11, further comprising a fourth connector having a first and a second end that are both one of male insertion portions or female receiving portions.

15. The modular implant system of claim 14 wherein one of the first and second ends of the fourth connector is larger than the other of the first and second ends of the fourth connector.

16. The modular implant system of claim 11 wherein in the first configuration, the first end of the second connector is directly attached to a first end of the first connector and the second end of the second connector is directly attached to the second implant member, and wherein a second end of the first connector is directly attached to the femoral knee prosthesis.

17. The modular implant system of claim 16 wherein in the second configuration, the first end of the third connector is directly attached to the first end of the first connector and the second end of the third connector is directly attached to the femoral hip stem, and wherein the second end of the first connector is directly attached to the femoral knee prosthesis.

18. A modular implant system for being positioned in an anatomy, comprising:

a first implant member having an articulating portion and operable to be positioned in the anatomy;

a second implant member operable to be positioned in the anatomy;

a third implant member having an articulating portion and operable to be positioned in the anatomy;

at least three connectors including a first, a second and a third connector, wherein each of the three connectors include a first end and a second end; and at least two of the connectors are interconnectable to form a connector assembly, wherein in a first configuration, the first and second connectors are interconnected between the first and second implant members and in a second configuration, the first and third connectors are interconnected between the first and third implant members; and a fourth connector having a first and a second end that are both one of male insertion portions or female receiving portions, wherein one of the first and second ends of the fourth connector is larger than the other of the first and second ends of the fourth connector;

wherein the first ends of the second and third connectors include the same connection region type while the second ends of the second and third connectors include distinct connection region types.

19. The modular implant system of claim 18, wherein the second implant member includes a stem operable to be positioned in the intramedullary canal of a bony structure.

20. The modular implant system of claim 19 wherein in the second configuration, the articulating portions of the first and third implant members provide articulating portions of a femoral knee implant and a femoral hip stem, respectively.

21. The modular implant system of claim 18 wherein the same connection region type includes one of male insertion portions or female receiving portions.

22. The modular implant system of claim 18 wherein the same connection region type includes tapering surfaces of identical geometries.

23. The modular implant system of claim 18 wherein the second connector and the second implant member are operable to be replaced from the first configuration with the third connector and the third implant member in the second configuration in a revision procedure while the first connector and the first implant member are left in an implanted position.

24. The modular implant system of claim 18 wherein in the first configuration, the first end of the second connector is directly attached to a first end of the first connector and the second end of the second connector is directly attached to the second implant member, and wherein a second end of the first connector is directly attached to the first implant member.

25. The modular implant system of claim 24 wherein in the second configuration, the first end of the third connector is directly attached to the first end of the first connector and the second end of the third connector is directly attached to the third implant member, and wherein the second end of the first connector is directly attached to the first implant member.

* * * * *

UNITED STATES PATENT AND TRADEMARK OFFICE
CERTIFICATE OF CORRECTION

Page 1 of 1

PATENT NO. : 7,998,218 B1
APPLICATION NO. : 11/049226
DATED : August 16, 2011
INVENTOR(S) : David R. Brown It is certified that error appears in the above-identified patent and that said Letters Patent is hereby corrected as shown below:

Column 1, line 25, "portion" should be --portions--.

Column 2, line 9, "and" should be --an--.

Column 2, line 41, "connections" should be --connection--.

Column 2, line 46, "connections" should be --connection--.

Column 2, line 64, after "second implant", insert --member--.

Column 3, line 41, after "to", insert --a--.

Column 3, line 42, after "connector", insert --of--.

Column 3, line 48, after "connector", insert --of--.

Column 4, line 36, "a kit a" should be --a kit as--.

Column 7, line 13, delete "degrees".

Column 7, line 36, "complimentary" should be --complementary--.

Column 8, line 50, "complimentary" should be --complementary--.

Column 10, line 1, "therefore" should be --therefor--.

Column 10, line 12, after "204", delete "that".

Column 11, line 52, "it's" should be --its--.

Column 12, line 64, "need" should be --needing--.

Column 14, line 19, "stems member" should be --stem members--.

Column 14, line 23, "provided" should be --provide--.

Column 14, line 34, "as a with" should be --as with--.

Signed and Sealed this
Eleventh Day of October, 2011

David J. Kappos
*Director of the United States Patent and Trademark Office*